United States Patent
Spranza et al.

(10) Patent No.: US 6,302,887 B1
(45) Date of Patent: Oct. 16, 2001

(54) HARDWARE FOR HIGH STRENGTH FASTENING OF BONE

(76) Inventors: Joseph John Spranza, 12493 Old Rough & Ready Hwy., Grass Valley, CA (US) 95945; Donald R. Huene, 201 N. Valeria, Fresno, CA (US) 93701

( * ) Notice: Subject to any disclaimer, the term of this patent is extended or adjusted under 35 U.S.C. 154(b) by 0 days.

(21) Appl. No.: 09/119,357

(22) Filed: Jul. 20, 1998

(51) Int. Cl.⁷ .................................................. A61B 17/86
(52) U.S. Cl. .............................. 606/73; 606/71; 411/338
(58) Field of Search .............................. 606/72, 73, 104, 606/60; 411/338, 339

(56) References Cited

U.S. PATENT DOCUMENTS

| | | | |
|---|---|---|---|
| 2,489,870 | * 11/1949 | Dzus | 606/73 |
| 2,760,488 | * 8/1956 | Pierce | 606/72 |
| 4,185,624 | * 1/1980 | Gentile | 606/73 |
| 5,217,462 | * 6/1993 | Asnis et al. | 606/73 |
| 5,250,049 | * 10/1993 | Michael | 606/72 |
| 5,498,265 | * 3/1996 | Asnis et al. | 606/73 |
| 5,683,460 | * 11/1997 | Persoons | 623/16 |
| 5,707,373 | * 1/1998 | Sevrain et al. | 606/72 |

* cited by examiner

*Primary Examiner*—David O. Reip

(57) ABSTRACT

A high strength fastener for bone fractures. This fastener consists of two members, a male and female. The male member has external machine screw threads that screw into matching internal threads in the female member at a predictable torque so that the force of fixation exerted upon the bone can be approximated by the installer. Because of the effective length of the threads, this fastener is easily adjusted to the proper length without cutting. Both members have a smooth shoulder region proximal to the heads and this shoulder region presents a low-stress bearing surface to each cortical wall. Each member has a head that fits rigidly into an installation tool providing for ease of insertion and fastening in the patient with minimal invasion and little periosteal stripping. Each head has a semi-spherical face that articulates with matching washers and plates, thus allowing the washer to assume the plane of the surrounding bone therefore distributing the load over a greater area.

4 Claims, 7 Drawing Sheets

HARDWARE FOR HIGH STRENGTH FASTENING OF BONE

BACKGROUND

1. Field of Invention

This invention relates to hardware for the surgical fastening of human and animal bone, especially when it is desirable to affect high strength fastening.

2. Discussion of Prior Art

In the field of Orthopedic surgery, the fastening together of bone fragments using hardware implanted under the soft tissue is known as "internal fixation". The cause of the bone fragmentation may be surgical osteotomy or traumatic fracture. Certain very serious considerations must be addressed when surgically fastening bone. It is necessary to fasten the bone fragments solidly together until the healing process, including osteogenesis, is completed. It is mandatory to affect a suitably tight fastening, so as to prevent excessive motion between the fragments. The repair must not fail; it must be solid enough to resist failure even with loading imposed by minor accidents. The force required to prevent excessive motion is often great. Such great forces may lead to a problem. Fastener forces can cause bone damage if the force is generally too high or if it is concentrated over too small an area, causing what may be called "point loading". In the process of doing the fastening, it is necessary to cause the least possible disturbance to the bone and associated tissue. The repair must involve minimal stripping of the soft tissue covering the bone.

There are essentially two types of bone, cortical and cancellous. Bones are living, "breathing" tissue. Covering the bone is a soft tissue, the periosteum. This covering contains blood vessels that convey food and oxygen to the bone, and carry waste materials and gasses away from the bone. The outer shell (cortical bone) of a bone is strong, hard and dense with a shear strength approximately ten times that of the inner bone (cancellous). The thickness of cortical bone in usually less than 10 mm while the diameter of the inner bone, cancellous, is commonly 25 to 30 mm. The cortical shell varies in thickness and strength, depending upon where it is located on the bone, and which bone it is. The history of use of the bone and the physical condition of the patient also affect the thickness and strength of the cortex. Cortical bone surrounds a softer, much less dense bone, the cancellous bone. Cancellous bone is somewhat spongy, due to physical design. It is very porous. Cancellous bone has fairly low shear strength and as stated above it is about one tenth as strong in shear as cortical bone. As humans and animals age, the percentage of cortical bone decreases while the percentage of cancellous bone increases. With all of the above considerations, bone fastening requires some very special techniques.

There are several methods used to fasten bone fragments together. Until this century, man had only one method for repairing bone fractures; closed reduction. The bones were anatomically re-aligned (fracture reduced) and the muscles and a splint (later a cast) held the bones in alignment and immobile until the fracture healed. Open fractures were virtually always fatal. In the last one hundred years man has been able to repair both open (compound) and seriously comminuted (splintered) closed fractures. In the last 50 years, surgeons use wire, smooth pins, rods and threaded fasteners, both with and without plating hardware. Because of specific loading limitations as well as other considerations, hardware such as washers and plates are used with fasteners to spread the load over a greater area. Plates may also serve to couple together an array of fasteners.

Wires are adequate for fracture fixation in a small percentage of bone fractures, preferred mostly when the fracture line is linear to the bone. Such fractures may occur when the hoop strength of the bone is exceeded, such as is generated when an object is driven into the medullary canal with so much force that it splits the bone outward. To fasten such a fracture, the wire is wound several times around the fractured bone, holding the fragments together, and the wire ends are twisted to secure the fastening. U.S. Pat. No. 5,697,934 describes a wire fastener. A variation on this wire technique employs a cable and special clip. The cable is tightened with a special tool, and the clip is crimped over the cable ends to secure them. Besides the limited strength of wire fixation, a further problem with this general type of fastening, called "cerclage wiring", is that it requires more surgical invasion and periosteal stripping than other methods of fastening. To expose naked bone the periosteum must be stripped off the bony surface. It is widely accepted that stripping soft tissue from bone must be kept to a minimum.

Smooth pins are sometimes used for fastening bones, but this is typically for low strength requirements and temporary fixation.

Rods, also called IM Nails, are used inside the bone, to restore shape. Such rods are variably locked (cross-fastened) to the bone with additional bone fastener hardware. Limitations with IM Nailing are that the installation requires additional major surgery, the rods prevent the bone from receiving strengthening exercise, and this "stress shielding" leads to bone weakening. Removal of the rods requires major surgery.

Threaded fasteners (bone screws) and washers are commonly used for fastening bone fragments together. There are many such fasteners on the market. The firms AO and Zimmer offer a number of threaded fasteners. Such fasteners work well in limited stress situations. Bone screws look rather like wood screws. The anchoring force of such screws comes from the shear strength and the hoop strength of the bone into which the screw is driven. The strength limitation encountered in fastening with bone screws is at least in part a function of physical properties of bones. As shown above, a large portion of any bone is cancellous bone, and cancellous bone is porous. The high-density portion of bone, the cortical bone, is of variable strength; therefore in many cases bone does not provide very good anchoring for threaded fasteners. Because of this, there are special screws with especially large threads (adding to the area) to catch more of this weak bone. (One such bone screw is described in U.S. Pat. No. 5,129,901) Such fasteners also rely upon the shear strength and hoop strength of the bone to anchor the threads of the screws. With advancing age, the reduction of cortical bone mass with the increase of cancellous bone mass reduces the ability of the patient's bone to anchor threaded fasteners. When the forces upon the bone (and thus the fastener) are great, the hoop strength and/or shear strength of the bone is exceeded, and the fastening fails (it pulls out allowing the bone fragments to separate)—catastrophically. A further disadvantage of bone screws which anchor into bone is the high and indeterminate torque of installation. A surgeon is never certain that the torque he is providing is tightening the bone fragments together (closing the fracture) or merely overcoming the torque required to drive the fastener further into the cortical bone.

Another fastener for bones is a bolt and nut. In the past, surgeons wanting high fastening strength had to use a bolt and a nut. The Webb Bolt, the Barr Bolt and the Zimmer Tibia Bolt exemplify this type of fastener. Because the available bolt length would not be exactly what was required, it was necessary to cut off the excess length of the bolt using a pinching action cutter. The cutting action left behind a sharp stump. Such cutting has some obvious disadvantages. 1) The cut destroys the thread profile, making disassembly and re-assembly of the bolt and nut difficult or impossible. 2) The cutting action imparts a force couple to the bolt, transmitting unacceptable forces to the surrounding bone. 3) The sharp edge remaining from the pinching off is harsh on the soft tissues, causing pain and trauma. 4) If this sharp edge is filed off, the debris is unacceptable to the body. A further disadvantage of the nut and bolt fastener is that the threads of the bolt pass unprotected through the cortical bone, and these unprotected threads are free to dig into the cortical bone, creating stress risers that can lead to failure. A further disadvantage of the nut and bolt fastener is that the washers were flat and fit flat against the bolt head and the nut. The washers could not tilt to spread the load evenly. Another disadvantage of this type of bolt and nut is that it was not cannulated. It could not be installed over a guide wire. Yet another disadvantage of this nut and bolt is found in the installation tooling. To afford truly minimally invasive installation, it is necessary to have complete control of the fastener until the surgeon is completely finished with the installation. The nut and bolt fastener could not be rigidly coupled to the installation tool. A surgeon could not readily insert the fastener accurately into a deep hole, and then direct it unerringly laterally and/or angularly. At the time of removal, the surgeon could not easily grasp the bolt or nut down deep in soft tissue and pull it from the bone.

OBJECTS AND ADVANTAGES

Accordingly, several objects and advantages of the present invention are:

a) To provide a high strength fastener that does not depend upon the strength of the bone being fastened;
b) To provide a fastener with a head on each end;
c) To provide a fastener that passes through both cortical walls with a smooth full size section to further enhance strength;
d) To provide a fastener that may be installed with minimal invasion;
e) To provide a fastener that may be rigidly coupled to installation tools, the coupling transmitting rotational, angular, lateral and reciprocal forces;
f) To provide a fastener that may be installed with little periosteal stripping;
g) To provide a fastener that may be installed over a guide wire;
h) To provide a fastener that has a dependable, predetermined torque required to screw it together, therefore enabling the surgeon to determine more accurately the fastening forces being generated by the fastener upon the bone.
i) To provide a fastener that requires no cutting to achieve correct length; and
j) To provide a fastener that increases bone contact, distributing the load over a greater area.

Other objects and advantages of this invention are to provide a fastening system that includes all hardware for minimally invasive installation of a fastener into difficult to access areas of the body.

Further objects and advantages of my invention will become apparent from a consideration of the drawings and ensuing description.

DESCRIPTION OF DRAWINGS

In the drawings, closely related figures have the same number but different alphabetic suffixes.

Figure 1:
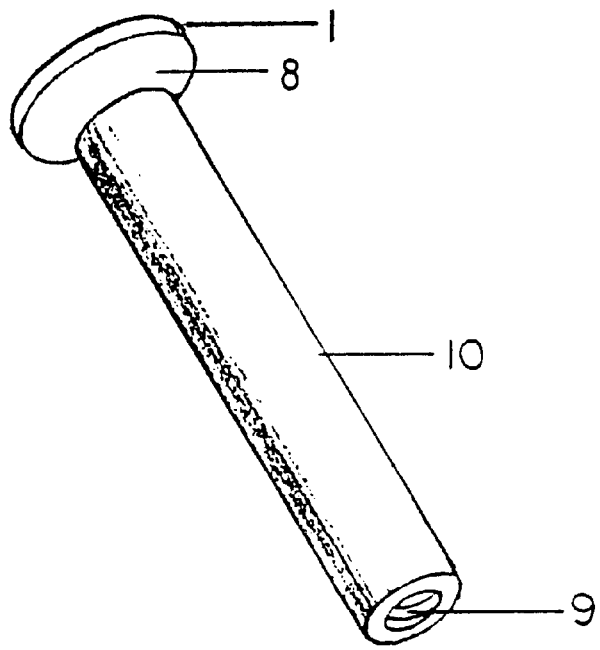
FIG. 1 shows the male and female members of the Fastener uncoupled.
Figure 1:
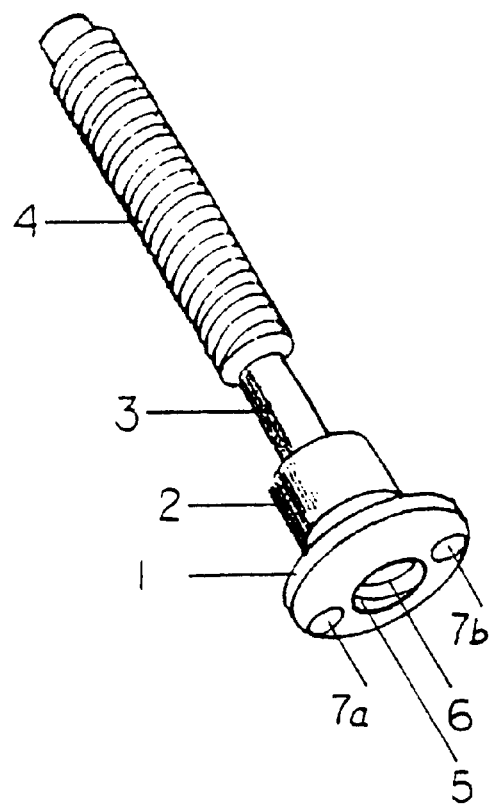

LIST OF REFERENCE NUMERALS 1. head of fastener
2. shoulder
3. glide shank
4. externally threaded portion
5. internally threaded portion of male member
6. through hole
7. holes a. & b. for receiving driving pins of installation tool
8. semispherical face of fastener members
9. internal screw thread of female member
10. female member shank
11. drawtube
12. partial cavity
13. drive pins a. & b.
14. knob for draw tube
15. handle of installation tool
16. specialized plate
17. washer lying flat against plane of local bone
18. fracture line of tibial buttress
19. semi-spherical concave seat of washer

SUMMARY

The hardware of this invention is a high strength fastener that does not depend for its holding force upon the strength of the bone. This fastener presents equal, full sized shoulders to both cortical walls, adding strength and decreasing the chances of stress risers. This fastener may quickly and easily be rigidly coupled to an installation tool, thereby enhancing installation into and removal from the bone. This fastener can be installed with minimal surgical invasion. Having a hole clear through all components, including the installation tools, this fastener can be installed over a guide wire. This fastener is inherently grossly adjustable for length, and therefore it is never necessary to cut it to length. This fastener may be screwed together with low and dependable torque and therefore the surgeon has a feel for the amount of force that is being exerted by the fastener upon the bone. This fastener is designed to allow washers to adapt to the local plane of the bone, thus precluding destructive point loading of the fastened bone.

DESCRIPTION OF INVENTION

The fastener of this invention, see FIG. 1, consists of a male member with a head 1, shoulder 2, glide shank 3, and threaded portion 4. A hole 6 of sufficient diameter runs clear through both male and female members (they are cannulated) allowing each member to fit over a guide wire.

Figure 2:
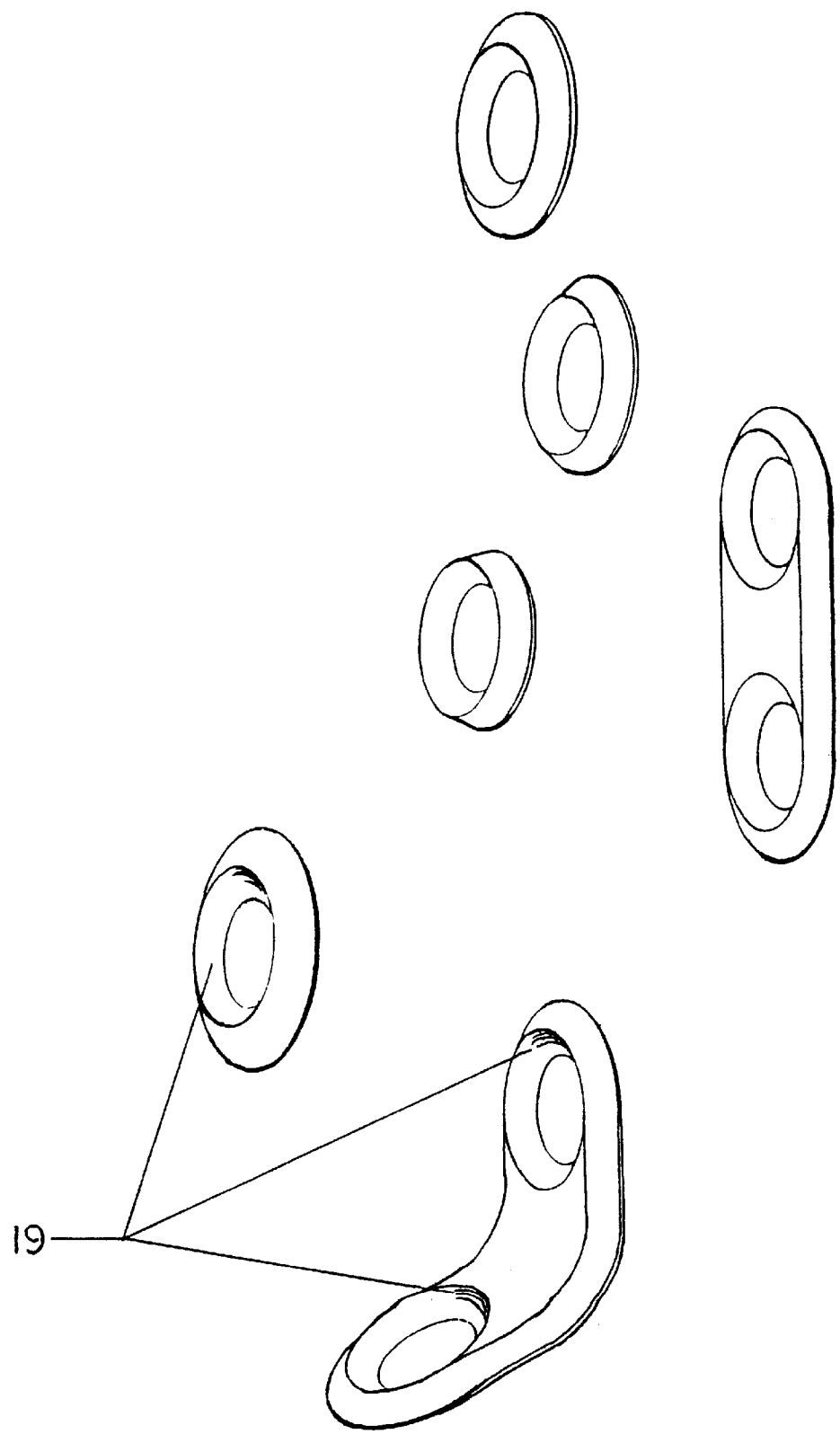
FIG. 2 shows several Washers and Plates that may be utilized with the Fasteners.
Figure 3:
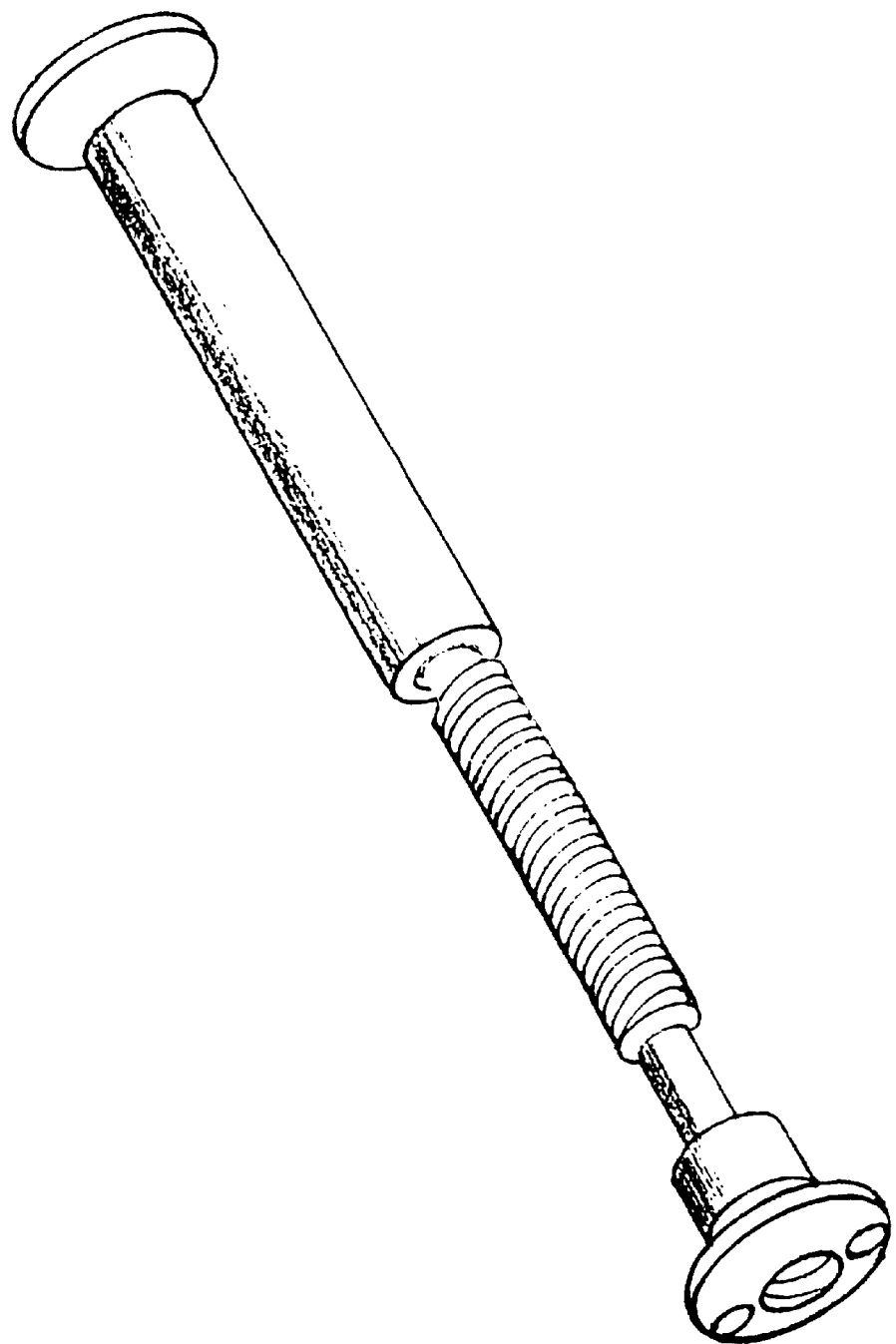
FIG. 3 shows the male and female members of the Fastener coupled by only half a thread.
Figure 4:
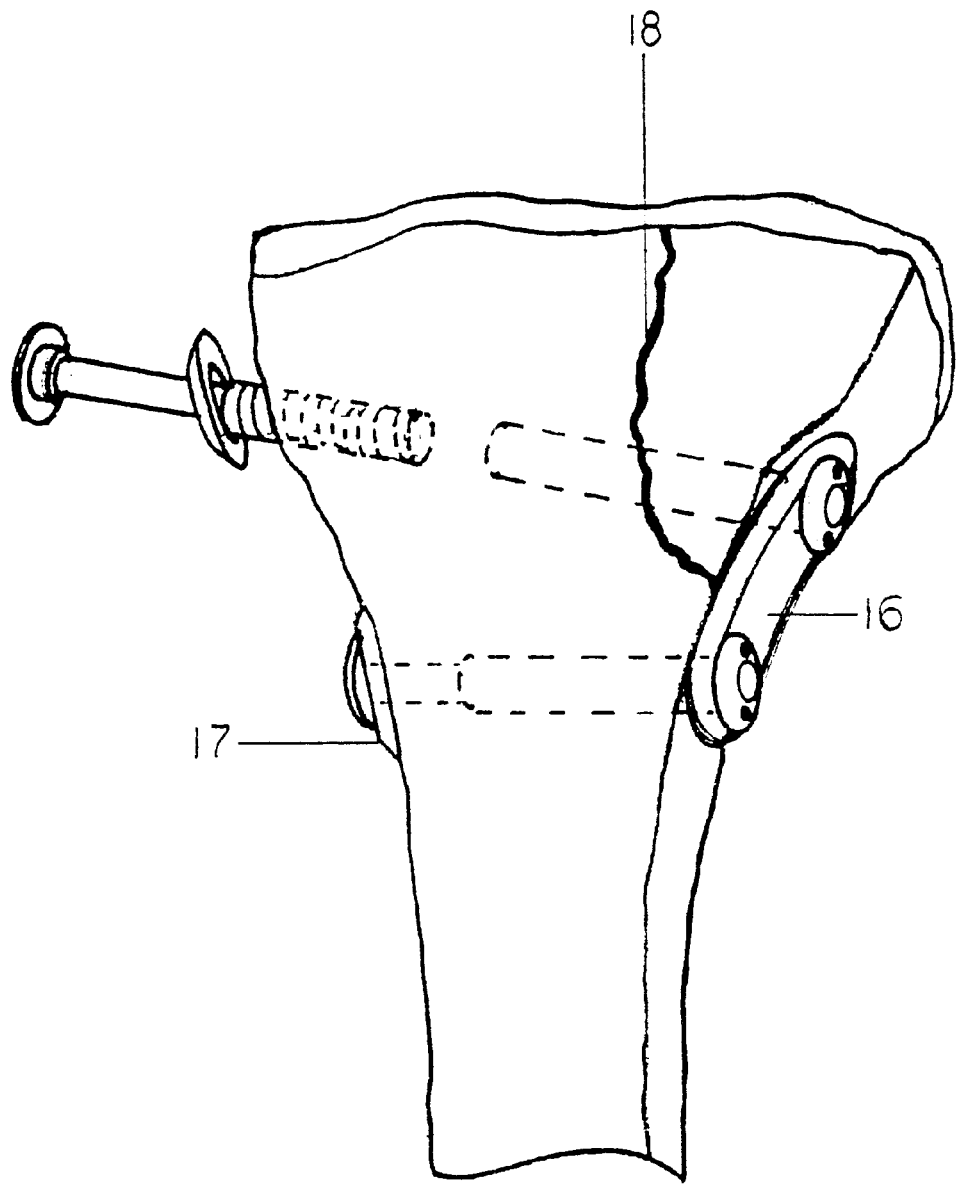
FIG. 4 shows a coupled Fastener, with a specialized multi-hole plate and an annular washer compressing a fractured tibial plateau buttress to the parent bone. A second fastener is not quite coupled.
Figure 5:
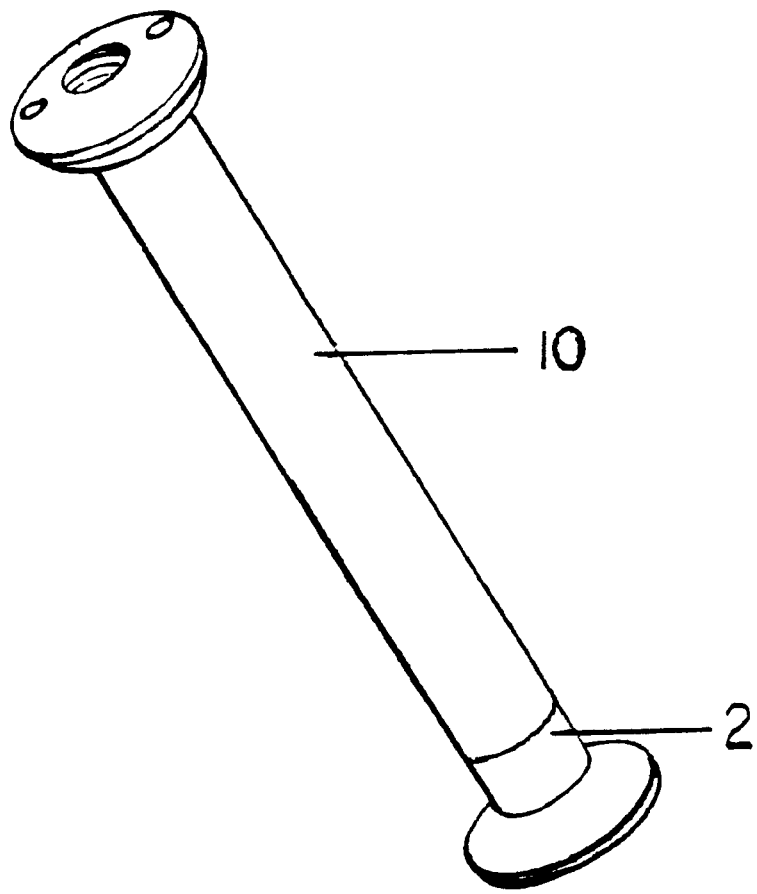
FIG. 5 shows a male and female fastener member completely coupled, shoulder to shank.
Figure 6:
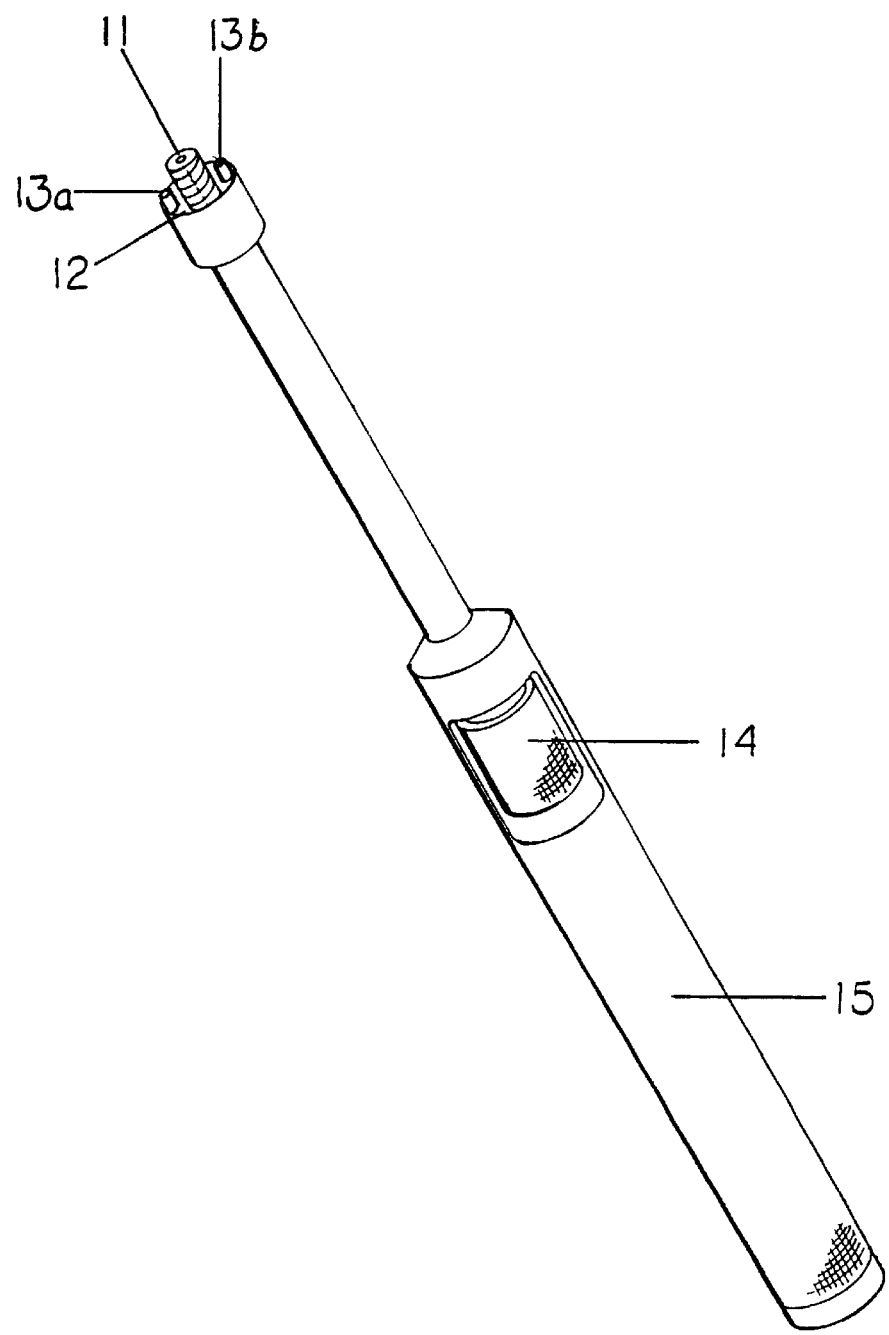
FIG. 6 shows an installation tool with the drive pins for rotation, the partial cavity for coupling and the drawtube for locking a fastener member to the tool.
Figure 7:
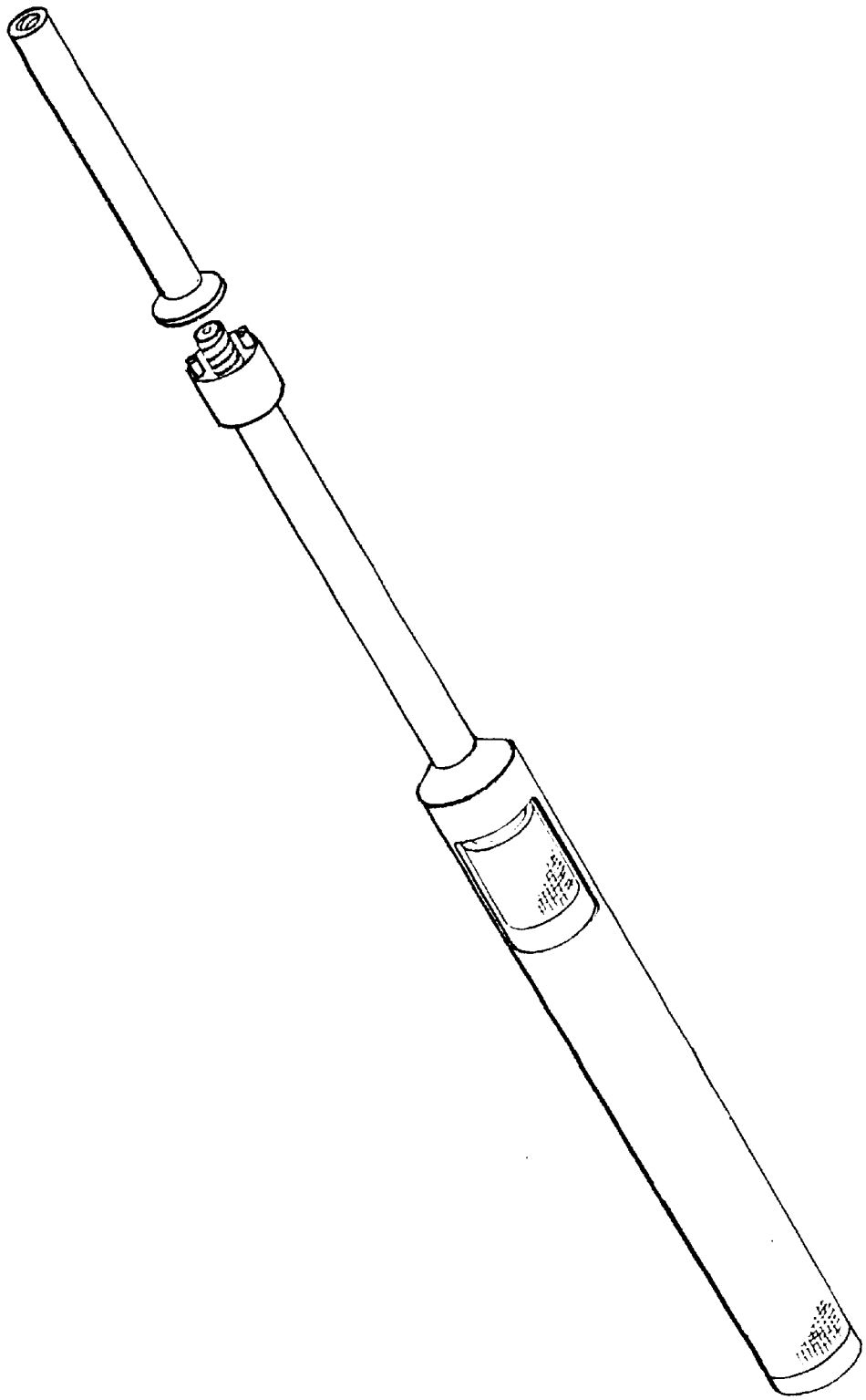
FIG. 7 shows a female member of the fastener aligned preparatory to attachment with a special installation tool.

The head is designed to provide for firm attachment to a special insertion tool, FIG. 6. This rigid attachment provides for turning, pulling, pushing and levering of the fastener by the insertion tool. In the preferred embodiment, FIG. 1, the fastener head is internally threaded 5, to receive a threaded male drawtube 11 protruding from the special insertion tool (See FIG. 6). A knob 14 connects to the drawtube 11 providing for rotation thereof. Two pins 13a and 13b protrude from the partial cavity 12 of the installation tool, and these pins mate into two holes 7a and 7b in the head of the fastener. The drawtube pulls the fastener head snugly into the partial cavity (12) wherein it is secured. The shank side face of the head has a semi-spherical shape 8, FIG. 1. See FIG. 7 showing a female member of the fastener properly aligned and close to being attached to an installation tool. The female member (see FIG. 1) of the fastener has a head similar to that of the male member. The shank is threaded through with an internal screw thread 9 that accepts with minimal clearance, the male's external screw thread 4. Maximum fastening strength is achieved with a minimum coupling length equal to one major diameter of the threads. See FIG. 3. But, the engagement of the male into the female threads may be continued until the shouldered portion of the male screw 2 abuts the tubular end of the female shank 10. See FIG. 5. Such an arrangement provides for telescoping like engagement of from practically two times the length of the individual screw members, down to only somewhat more than a single member length, thus providing for almost a two times length adjustment. No cutting of excess length is necessary to achieve a proper length of the fastener to the bone. Bone fragments may be pulled together after coupling only a few threads of this fastener. Further engagement of the male and female members is continued by screwing the members further together until sufficient force is imparted by the fastener to the bone to immobilize (rigidly fixate) the bone fragments. See FIG. 4 showing a fractured bone and two fasteners. The fracture line is 18. The lower fastener is engaged adequately enough to fasten the distal portion of the lateral buttress bone fragment. The second fastener is not yet coupled. To spread the load of the fastening forces, special washers of the desired size and shape may be utilized. See FIG. 2 and FIG. 4. In FIG. 4, note that washer 17 is gimbaled (tilted) at an angle to the fastener linear axis and is lying flat against the surface of the bone immediately surrounding the fastener. The plate 16 coupling two fasteners is pre-curved fit to the bone surface. The washers and plates of this invention are free to "gimbal" (tilt) under each fastener head because each washer and plate have matching semispherical seats FIG. 2. 19 around their holes that mate with the semispherical face 8 (FIG. 1) on the head. Therefore, the washer may lie flat against (gimbal) the plane of the bone immediately surrounding the fastener. This precludes point loading the bone by the fastener washers, which, were it to occur, would lead to localized necrosis and failure of the bony tissue.

From the description above, a number of advantages of my fastener become evident:

a. The surgeon can rely on this fastener not to pull out of the bone in high strength requirements, because the male member is threaded into the female fastener member and the strength of fastening does not depend upon the strength of the bone.

b. The fastener has a head on each end therefore excessive hoop stresses are not generated.

c. The smooth full sized shoulders on this fastener present a good bearing surface to the bone cortical walls.

d. This fastener may be installed percutaneously; being drilled clear through (cannulated) it may pass over a guide wire, and it attaches rigidly to installation tools.

e. The amount of torque required to tighten this fastener is essentially constant and it is not a function of the depth and strength of the bone, so a surgeon can feel when it is tight.

f. The surgeon does not need to cut this fastener to achieve a correct length; it is very adjustable and has no sharp edges.

g. The washers and plates are free to lie flat against the bone, to distribute the load and not to dig in causing unhealthy point loading of the bony tissue.

OPERATION OF INVENTION

Perform adequate pre-operative planning to determine reasonable screw placement and angle. Reduce the fracture for the optimum anatomic fit. Clamp the reduction while observing with fluoroscopic visualization. Insert a guide wire through the reduced fragments. The placement of the guide wire is to be in the center of the desired fastening. Separate the overlying tissue. Use a knife to cut the periosteum around the guide wire. Using a cannulated drill bit, drill over the guide wire bi-cortically through the bone. Drill the hole of adequate diameter to accept the diameter of the shank of the female member fastener. Assemble the fastener members to the special installation tools by aligning the pins 13a & 13b with holes 7a & 7b and pushing the respective member into the partial cavity 11. Turn the knob 14 to screw the drawtube 11 into the threaded hole 5 on the head of the fastener member, (FIG. 1 and FIG. 6) thus affecting a rigid attachment of each member to each installation tool. See FIG. 7 to see alignment of element with special installation tool. Assemble the appropriate washers (see FIG. 2) and/or plates onto each fastener member. The selection of an appropriate washer is made talking into consideration both the quality of the bone and the anticipated loading on the bone. Heavy loading and weak bone stock require a larger washer to distribute the load over a greater area. See FIG. 4. which shows that an appropriate plate is selected taking into consideration the array of fasteners and the curve of the bone. Insert the female fastener member over the guide wire (guide wire passes through hole 6) on one side, either lateral or medial, of the bone. Since the fastener is rigidly attached to the installation tool, insertion is easy and quick. See FIG. 7. The installation tool is long enough to push the fastener member down through considerable tissue depth. The rigid attachment of the fastener members to the tools enables the surgeon to probe and push the fastener to work it through the separated soft tissue and then to penetrate the hole in the bone. Push the female fastener member firmly down into the hole so that the washer or plate is seated against the proximal cortex. The close fit of the full size shank on the female fastener member to the hole in the bone will nicely hold the bone fragments in place. Next, insert (from the opposite side of the bone) the male fastener member over the guide wire in a manner similar to that used to insert the female member. When the externally threaded portion enters the hole in the bone, align the linear axis of the male member with that of the female member. It is easy to determine the co-linearity of the male and female members, since each is linear to its respective installation tool. Merely observe that the installation tool handles FIG. 6, 15 are in a straight line. Pushing lightly on each handle, rotate respectively clockwise each handle and couple the male and female members. Continue to engage the members by screwing them together until adequate fixation is achieved. The clamping force of the fasteners on the bone is more precise with the system of this invention than with bone screws due to the fact that the torque required to screw the members together is essentially constant and therefore any additional force is being exerted upon the bone. Use fluoroscopic visualization to ascertain desirable washer and/or plate attitude and fastening force. When adequate fixation has been achieved, remove each installation tool by turning the knob 14 anti-clockwise and thereby uncoupling the installation tool from the fastener head.

CONCLUSION, RAMIFICATIONS AND SCOPE OF INVENTION

Thus, the reader will see that the fastener of this invention provides a high strength fastener, independent of the strength of the bone. This fastener has a head at both cortexes. This fastener presents smooth full size shoulders to both cortical walls so as to prevent stress risers. The installation of the fastener of this invention may be done with minimal surgical invasion. A minimum of periosteal stripping is required. No cutting of the fastener for length adjustment is required; the fastener of this invention is inherently widely adjustable. The fastener of this invention has a dependable torque of assembly therefore the surgeon has a feel to approximate the amount of force that is being imparted to the bone by the fastener. This fastener system is cannulated and may be installed over a guide wire. This fastener couples rigidly to installation tooling, providing for precise positioning and control of installation. This hardware is designed such that there is no point loading of the bony tissue: the associated washers and/or plates spread the load and assume an appropriate angle, tilting to match the local plane of the bone.

While my above description contains many specificities, these should not be construed as limitations on the scope of this invention, but rather as an exemplification of one preferred embodiment thereof. Many other variations are possible. For example, the coupling of the installation tool to the fastener member could be accomplished by a push and quarter turn lock engagement. The heads may have a hexagonal receptacle singularly or in addition to the holes (7a & b) to allow the use of a hex key for removal.

The heads may have one or more slots, singularly or in addition to the holes (7a & b) to allow a straight bladed screwdriver to be used in removal. The heads may have a hexagonal shaped girdle to allow the use of a socket wrench in removal. The elongate member may be other than circular in cross section; it could be elliptical, square, hexagonal, and so on. The fastener might be made of materials other than metal; these alternate materials may include plastic or (PLA) polylactic acid.

Accordingly, the scope of the invention should be determined not by the embodiment(s) illustrated, but by the appended claims and their legal equivalents.

I claim:

1. A bone fastener system for securely fastening bony and soft tissue, comprising:

a bone fastener, the bone fastener comprising a male component and a female component, wherein both the male and female components each have a head portion with an inner face which is convexly semi-spherical and an outer face which is convexly semi-spherical, the male component further having an elongated body portion, the body portion of the male component being cannulated and having external threads, the female component further having an elongated body portion, the body portion of the female component having an axial throughbore with internal threads, wherein the external threads of the male component correspond to and are configured to mate with the internal threads of the female component;

at least one washer member, the washer member comprising a concavely semi-spherical recess configured to receive the inner face of at least one of the male component and female component; and an installation tool, the installation tool configured for coupling with the head portion of the male component.

2. The bone fastener system of claim 1, wherein the washer member comprises a plate member having at least two concavely semi-spherical recesses.

3. The bone fastener system of claim 1, wherein the head portion of the male component comprises an internally threaded axial bore and at least two drive holes spaced from the axial bore.

4. The bone fastener system of claim 3, wherein the installation tool comprises a concavely semi-spherical socket, an externally threaded drawtube, and at least two drive pins, wherein the semi-spherical socket and the at least two drive pins are configured to mate with the semi-spherical head and the at least two drive holes of the head portion of the male component, and wherein the externally threaded drawtube is configured to mate with the internally threaded axial bore in the head portion of the male component.

* * * * *